United States Patent [19]

Isshiki et al.

[11] Patent Number: 4,620,033

[45] Date of Patent: Oct. 28, 1986

[54] PROCESS FOR PRODUCING CARBOXYLIC ACIDS

[75] Inventors: Tomiya Isshiki, Tokyo; Yasuhiko Kijima; Yuh Miyauchi, both of Chiba; Takao Kondo, Tokyo, all of Japan

[73] Assignee: Mitsubishi Gas Chemical Company, Inc., Tokyo, Japan

[21] Appl. No.: 697,696

[22] Filed: Feb. 4, 1985

Related U.S. Application Data

[63] Continuation of Ser. No. 369,639, Apr. 19, 1982, abandoned.

[30] Foreign Application Priority Data

Apr. 21, 1981 [JP] Japan .................................. 56-60418
Jul. 20, 1981 [JP] Japan ................................ 56-113159

[51] Int. Cl.$^4$ ...................... C07C 51/12; C07C 53/08

[52] U.S. Cl. .............................. 562/519; 260/410.9 R; 260/413; 560/232; 562/406; 562/497; 562/517

[58] Field of Search ............... 562/519, 497, 406, 517; 260/413, 410.9 R; 560/232

[56] References Cited

U.S. PATENT DOCUMENTS 4,134,912  1/1979  Naglieri et al. ...................... 562/497
4,336,399  6/1982  Isshiki et al. ........................ 562/519

Primary Examiner—Werren B. Lone
Attorney, Agent, or Firm—Wenderoth, Lind & Ponack

[57] ABSTRACT

A process for producing a carboxylic acid which comprises reacting a hydrocarbyl alcohol with carbon monoxide in the presence of a metal catalyst selected from nickel or cobalt, a halide and a specific promoter is disclosed. According to the present invention, formation rate of carboxylic acid is high.

17 Claims, No Drawings

PROCESS FOR PRODUCING CARBOXYLIC ACIDS

This application is a continuation of now abandoned application Ser. No. 369,639, filed Apr. 19, 1982.

BACKGROUND OF THE INVENTION

This invention relates to a process for producing a carboxylic acid which comprises reacting a hydrocarbyl alcohol with carbon monoxide.

A process for producing a carboxylic acid by carbonylation reaction of an alcohol, such as a process for producing acetic acid from methanol and carbon monoxide was known.

In the prior art, the known catalysts for producing carboxylic acids from alcohols and carbon monoxide include the following:

(i) a catalyst comprising a noble metal belonging to Group VIII of the Periodic Table, such as rhodium, a halide and a third component as disclosed in Japanese Patent Publication (Kohkoku) Nos. 3331/1972; 3332/1972; 3333/1972; 3334/1972; 3335/1972; 3336/1972 and 3337/1972, and (ii) a catalyst comprising nickel or cobalt, halide and a third component as disclosed in U.S. Pat. Nos. 2,729,651; 2,727,902 and 4,134,912 and German Pat. Nos. 921,938; 933,148 and 947,469, Japanese Patent Publication (Kohkai) No. 84912/1978 and Japanese Patent Publication (Kohkai) Nos. 59211/1979; 63002/1979 and 66614/1979 assigned to the assignee of this invention.

However, catalyst (i) contains expensive rhodium as shown in Hydrocarbon Processing 54, June 83 (1975).

In case of producing carboxylic acids from hydrocarbyl alcohols and carbon monoxide by using a rhodium catalyst, a rhodium complex has to be prevented from being reduced to metallic rhodium under a reducing atmosphere as disclosed in KAKTAF 29 (5) page 376 (1975) or the rhodium component has to be prevented from being scattered from the reaction system during the operation of separating the product as disclosed in Japanese Patent Publication (Kohkai) No. 99204/1978.

The method using component (ii), such as described in U.S. Pat. No. 4,134,912 and Japanese Patent Publication (Kohkai) No. 84912/1978, is attractive in that it uses an inexpensive nickel catalyst, but in this method, as much as about 40% of an iodide cocatalyst is present in the reaction system. Further, the method requires a large amount of ligand typified by triphenylphosphine, but no corresponding improvement in the yield of the reaction product and reaction rate is achieved. As another disadvantage, the ligand used in a large amount is sparingly soluble in the reaction liquor and recycling of the catalyst and cocatalyst that is necessary in continuous operation is very difficult, if not impossible. At the same time, the ligand is labile and its activity is rapidly reduced. For these reasons, the second method has not been used on an industrial scale.

SUMMARY OF THE INVENTION

The present inventors carried out research to increase the rate of reaction between a hydrocarbyl alcohol and carbon monoxide, to use a reaction catalyst under milder reaction conditions and to improve the life of catalyst. As a result we found a process for producing a carboxylic acid from a hydrocarbyl alcohol and carbon monoxide in the presence of nickel or cobalt catalyst, a halide and a specific promoter.

This invention relates to a process for producing a carboxylic acid which comprises reacting a hydrocarbyl alcohol with carbon monoxide in the presence of (A) a catalyst comprising at least one material selected from the group consisting of nickel, cobalt, nickel compounds, cobalt compounds and mixtures thereof, (B) at least one halide selected from the group consisting of bromides, iodides and mixtures thereof and (C) a promoter characterized in that said promoter comprises:

component (i) composed of one or more materials selected from the group consisting of metals belonging to Group IVB of the Periodic Table, compounds of the metals and mixtures thereof, and component (ii) selected from (a) at least one organic nitrogen compound and (b) one or more materials selected from the group consisting of metals belonging to Group IA and IIA of the Periodic Table, compounds of the metals and mixtures thereof.

DETAILED DESCRIPTION OF THE INVENTION

By the "Periodic Table" given in the specification and the claims is meant Periodic Table in "Shin Jikken Kagaku Kohza" vol. 12, 1976 pages 4–5 published by the Japan Chemical Association.

The catalysts employed in the practice of this invention include organic or inorganic nickel compounds and organic or inorganic cobalt compounds, and metallic nickel or cobalt. Examples of nickel, cobalt and nickel and cobalt compounds include nickel powder; nickel compounds, such as nickel acetate, nickel iodide, nickel acetylacetonate, nickel tetracarbonyl, nickel dicarbonyl, and tetramethyl ammonium nickel iodide; cobalt powder and cobalt compounds, such as cobalt hydroxide, cobalt carbonate, cobalt acetylacetonate, cobalt iodide, cobalt acetate, dicobalt octacarbonyl, tetracobalt dodecacarbonyl, and cobalt hydride tetracarbonyl. One material or a mixture of two or more materials may be used as the catalyst. Nickel powder or nickel compounds are preferable as a catalyst.

Halides employed together with the catalyst include bromides, iodides or mixtures thereof. Examples of the halides include alkyl halide, such as methyl iodide, acid halogenides, such as acetyl iodide, or hydrogen halides, such as hydrogen iodide, or mixtures thereof. The halide may be added to a reaction medium as it is. Materials which can convert to an alkyl halide, an acid halogenide or hydrogen halide can be used as a halide constituting the catalyst of this invention. Examples of the materials which convert to an alkyl halide, an acid halogenide or a hydrogen halide by reacting with other components in the reaction medium include inorganic halides, such as alkali metal halides, such as lithium, sodium or potassium halides; alkaline earth metal halides, such as magnesium or calcium halides; metal halides such as aluminum, zinc, copper, lanthanum, or cerium halides; or bromine or iodine. When halides of metals belonging to Groups IA, IIA, or IVB of the Periodic Table are used as a halide constituting the catalyst of this invention, they also serve as a component constituting the promoter of this invention. Of the halides, methyl halides, such as methyl iodide, are preferable, because the use of these compounds makes easy the selection of corrosion-resistant reactor and separation of the reaction product from the reaction mixtures and purification of the reaction product.

The amount of the catalyst employed in this invention may be in the range of $10^{-6}$ mol–5 mol, preferably $10^{-4}$ mol–2 mol, more preferably $10^{-3}$ mol–1 mol and most preferably $5\times10^{-3}$ mol–0.2 mol per 1 liter of a reaction solution in terms of metal.

The amount of the halide employed as one component of the catalyst may be in the range of from $10^{-3}$ mol–15 mol, preferably $10^{-2}$ mol–8 mol and more preferably $10^{-1}$ mol–4 mol, most preferably $2\times10^{-1}$ mol–2.5 mol per 1 liter of a reaction solution in terms of halogen atom.

The promoters employed in the practice of this invention comprises:

component (i) composed of one or more materials selected from the group consisting of metals belonging to Group IVB of the Periodic Table, compounds of the metals and mixtures thereof, and component (ii) selected from (a) at least one organic nitrogen compound and (b) one or more materials selected from the group consisting of metals belonging to Groups IA and IIA of the Periodic Table, compounds of the metals and mixtures thereof.

As described before, the low solubility of organic phosphorus compounds such as triphenylphosphine makes the recycling of the catalyst system difficult, and its low stability shortens the life of the catalyst. These defects are significantly eliminated by combining component (i) with component (ii)(a) or with components (ii)(a) and (b) using an organic nitrogen compound. Better results are obtained by combining component (i) with component (ii)(b) free from an organic ligand, and high catalytic activity, long life and high solubility are achieved.

Preferable metals of Group IVB and compounds of the metals which are usable as component (i) include silicon, germanium and tin, and compounds of the metals. Tin and tin compounds are most preferable.

Preferable metals of Group IA and compounds of the metals which are usable as component (ii)(b) include lithium, sodium, potassium, rubidium and cesium, and compounds of the metals. Lithium, rubidium and cesium, and compounds of these metals are more preferable; and lithium and its compounds are most preferable.

Preferable metals of Group IIA and compounds of the metals which are usable as component (ii)(b) include beryllium, magnesium, calcium, strontium and barium and compounds of the metals. Magnesium, calcium, strontium and barium and compounds of the metals are more preferable; and calcium and strontium and compounds of these metals are most preferable.

By combining component (i) with at least one metal selected from the group consisting of groups IA and IIA typified by lithium or metal compounds thereof, a remarkable increase in the catalytic activity, i.e. the formation rate of carboxylic acid (in grams) per gram of elemental catalytic metal per gram of elemental halogen per hour is obtained.

The metals belonging to Groups IA, IIA, and IVB of the Periodic Table which are usable as the promoter may be used in form of element or in form of compounds. For example, they can be used as metal itself or Raney metals, or finely divided particles of the metals, or as metal compounds, such as carbonates, oxides, hydroxides, nitrates, sulfates, phosphates, halides, cyanides, thiocyanides, sulfonates, $C_1$–$C_5$ lower alkoxides, such as methoxides and ethoxides, phenoxide, metal carboxylates derived from $C_1$–$C_{20}$ alkanoic acids, oxyhalides, hydrides, nitrites, sulfites, phosphites, acetylacetonates and sulfides of metals, or metal compounds coordinated with ammonia, cyanide, amines or amino acids, or organic metal compounds having phenyl group or alkyl group.

Metals of Group IVB and compounds of the metals include, for example $H_2SiO_3$, $H_4SiO_4$, $SiHBr_3$, $SiHCl_3$, $SiHF_3$, $SiHI_3$, $Si$, $Si(OCH_3)_4$, $Si_2Br_6$, $SiBr_4$, $SiBrH_3$, $SiBrCl_3$, $SiBr_2Cl_2$, $SiBr_3Cl$, $Si_2Cl_6$, $SiCl_4$, $SiClH_3$, $SiF_4$, $SiH_4$, $Si_2H_6$, $Si_3H_8$, $Si_4H_{10}$, $SiI_2$, $Si_2I_6$, $SiI_4$, $SiICl_3$, $SiO_2.XH_2O$, $SiO_2$, $Si_2OCl_6$, $SiS$, $SiS_2$, $Ge$, $GeBr_4$, $GeCl_2$, $GeCl_4$, $GeHCl_3$, $GeF_4.3H_2O$, $GeH_4$, $GeI_2$, $GeI_4$, $GeO$, $GeO_2$, $GeOCl_2$, $GeS$, $GeS_2$, $Sn$, $SnBr_4$, $SnCl_4$, $SnF_4$, $SnI_4$, $SnO_2$, $SnOCl_2$, $2SnO_2.P_2O_5.10H_2O$, $SnP$, $Sn(SO_4)_2.2H_2O$, $SnS_2$, $SnBr_2$, $SnCl_2$, $SnF_2$, $Sn(OH)_2$, $SnI_2$, $SnC_2O_4$, $SnO$, $SnO.SnCl_2.3H_2O$, $SnSO_4$, $SnS$, $Sn(CH_3)_4$, $Sn(CH_3)_2$, $Sn(C_2H_5)_4$, $Sn(C_6H_5)_4$, $(C_3H_7)_2SnH_2$, $(CH_3)_2SnI_2$, $(CH_3)_2SnCl_2$, $Sn(C_2H_5)_2$, $(C_4H_9)_2SnCl_2$, $(C_2H_5)_2SnI_2$, $(CH_3)_3SnCl$, $(C_4H_9)_2SnH_2$, $(C_3H_7)_2SnI_2$, $(CH_3)_3(CH_2I)Sn$, $(C_4H_9)_3SnCl$, $(C_4H_9)_2SnI_2$, $(C_2H_9)_3SnCl$, $(C_4H_9)_3SnH$, $(C_2H_5)_3SnH$, $(C_6H_5CH_2)_3SnCl$, $Sn(C_2H_3O_2)_2$, $Sn(C_2H_3O_2)_4$, $SnHPO_4$.

Metals of Group IA and compounds of the metals include, for example, $Li$, $LiC_2H_3O_2.2H_2O$, $LiAlO_2$, $LiNH_2$, $LiBO_2$, $Li_2B_4O_7.5H_2O$, $LiBr$, $LiBr.2H_2O$, $Li_2CO_3$, $LiHCO_3$, $LiClO_3$, $LiClO_3.0.5H_2O$, $LiCl$, $Li_3C_6H_5O_7.4H_2O$, $Li_2S_2O_6.2H_2O$, $LiF$, $Li_2[SiF_6].2H_2O$, $LiHCO_2.H_2O$, $LiH$, $LiOH$, $LiOH.H_2O$, $LiI$, $LiI.3H_2O$, $LiNO_3$, $LiNO_3.3H_2O$, $LiNO_2.H_2O$, $Li_2C_2O_4$, $LiHC_2O_4.H_2O$, $Li_2O$, $LiClO_4$, $LiClO_4.3H_2O$, $LiMnO_4$, $LiH_2PO_4$, $Li_3PO_4$, $Li_3PO_4.12H_2O$, $Li_2SiO_3$, $Li_4SiO_4$, $Li_2SO_4$, $Si_2SO_4.H_2O$, $LiHSO_4$, $Li_2S$, $Li_2SO_3$, $Rb$, $RbBrO_3$, $RbBr$, $RbBr_3$, $Rb_2CO_3$, $RbHCO_3$, $RbClO_3$, $RbCl$, $RbF$, $RbH$, $RbOH$, $RbIO_3$, $RbI$, $RbI_3$, $RbNO_3$, $Rb_2O$, $Rb_2O_2$, $Rb_2O_3$, $Rb_2O_4$, $RbClO_4$, $RbIO_4$, $RbMnO_4$, $Rb_2SeO_4$, $Rb_2SO_4$, $Rb_2S$, $Rb_2S.4H_2O$, $Rb_2S_3$, $Rb(C_2H_3O_2)$, $Cs$, $CsBrO_3$, $CsBr$, $CsBr_3$, $Cs_2CO_3$, $CsHCO_3$, $CsCl$, $CsCN$, $CsF$, $CsH$, $CsOH$, $CsIO_3$, $CsI$, $CsI_3$, $CsNO_3$, $CsNO_2$, $Cs_2O$, $Cs_2O_2$, $Cs_2O_3$, $Cs_2O_4$, $CsClO_4$, $CsIO_4$, $CsMnO_4$, $Cs_8SiW_{12}O_{42}$, $Cs_2SO_4$, $CsHSO_4$, $Cs_2S.4H_2O$, $Cs_2S_2$, $Cs_2S_2.H_2O$, $Cs_2S_3$, $Cs_2S_5$, $CsHC_4H_4O_6$, $Cs(C_2H_3O_2)$.

The metals of Group IIA and compounds of the metals include, for example $Mg$, $Mg(C_2H_3O_2)_2$, $Mg(C_2H_3O_2)_2.4H_2O$, $MgO.Al_2O_3$, $MgCl_2.NH_4Cl.6H_2O$, $MgNH_4PO_4.6H_2O$, $MgSO_4.(NH_4)_2SO_4.6H_2O$, $Mg(BO_2)_2.8H_2O$, $Mg(BrO_3)_2.6H_2O$, $MgBr_2$, $MgBr_2.6H_2O$, $MgCO_3$, $MgCO_3.3H_2O$, $3MgCO_3.Mg(OH)_2.3H_2O$, $Mg(ClO_3)_2.6H_2O$, $MgCl_2$, $MgCl_2.6H_2O$, $MgF_2$, $Mg[SiF_6].6H_2O$, $Mg(OH)_2.Mg(H_2PO_2)_2.6H_2O$, $Mg(IO_3)_2.4H_2O$, $MgI_2$, $Mg(NO_3)_2.6H_2O$, $Mg_3N_2$, $MgC_2O_4.2H_2O$, $MgO$, $Mg(ClO_4)_2.6H_2O$, $Mg(MnO_4)_2.6H_2O$, $Mg_3(PO_4)_2.4H_2O$, $Mg_3(PO_4)_2.8H_2O$, $MgHPO_4.3H_2O$, $MgHPO_4.7H_2O$, $Mg_2P_2O_7$, $Mg_2P_2O_7.3H_2O$, $MgHPO_3.3H_2O$, $MgCl_2.KCl.6H_2O$, $MgSO_4.K_2SO_4.6H_2O$, $MgCl_2.NaCl.H_2O$, $MgSO_4$, $MgSO_4.7H_2O$, $MgS$, $MgSO_3.6H_2O$, $Mg(C_4H_4O_6).5H_2O$, $MgS_2O_3.6H_2O$, $Ca$, $Ca(C_2H_3O_2)_2.H_2O$, $Ca(AlO_2)_2$, $CaO.Al_2O_3.2SiO_2$, $CaNH_4AsO_4.6H_2O$, $CaNH_4PO_4.7H_2O$, $Ca_3(AsO_4)_2$, $Ca(BO_2)_2.2H_2O$, $CaB_6$, $Ca(BrO_3)_2.H_2O$, $CaBr_2$, $CaBr_2.6H_2O$, $CaC_2$, $CaCO_3$, $Ca(ClO_3)_2.2H_2O$, $CaCl_2$, $CaCl_2.H_2O$, $CaCl_2.6H_2O$, $Ca_3(C_6H_5O_7)_2.4H_2O$, $Ca(CN)_2$, $Ca(CN)_2$, $CaS_2O_6.4H_2O$, $CaF_2$, $Ca[SiF_6]$, $Ca[SiF_6].2H_2O$, $Ca(HCO_2)_2$, $CaH_2$, $Ca(SH)_2.6H_2O$, $Ca(OH)_2$, $Ca(ClO)_2.4H_2O$, $Ca(IO_3)_2$, $CaI_2$, $CaI_2.6H_2O$, $Ca(C_3H_5O_3)_2.5H_2O$, $CaO.MgO.2CO_2$, $CaO.MgO.2SiO_2$, $CaMoO_4$, $Ca(NO_3)_2$, $Ca(NO_3)_2.4H_2O$, $Ca_3N_2$, $Ca(NO_2)_2.H_2O$, $CaC_2O_4$, $CaO$, Ca(MnO$_4$)$_2$.4H$_2$O, CaO$_2$.8H$_2$O, CaHPO$_4$.2H$_2$O, Ca$_2$P$_2$O$_6$.2H$_2$O, Ca(PO$_3$)$_2$, Ca(H$_2$PO$_4$)$_2$.H$_2$O, Ca$_2$P$_2$O$_7$, Ca$_2$P$_2$O$_7$.5H$_2$O, Ca$_3$(PO$_4$)$_2$, 2CaHPO$_3$.3H$_2$O, Ca(H$_2$PO$_2$)$_2$, CaK$_2$(SO$_4$)$_2$.H$_2$O, CaSiO$_3$, CaSi$_2$, CaSO$_4$.2Na$_2$SO$_4$.2H$_2$O, CaSO$_4$, CaSO$_4$.2H$_2$O, CaSO$_4$.0.5H$_2$O, CaS, CaSO$_3$.2H$_2$O, CaC$_4$H$_4$O$_6$.4H$_2$O, CaCS$_3$, Ca(SCN)$_2$.3H$_2$O, CaS$_2$O$_3$.6H$_2$O, CaWO$_4$, Sr, Sr(C$_2$H$_3$O$_2$)$_2$, SrB$_4$O$_7$.4H$_2$O, Sr(BrO$_3$)$_2$.H$_2$O, SrBr$_2$, SrBr$_2$.6H$_2$O, SrCO$_3$, Sr(ClO$_3$)$_2$, Sr(ClO$_3$)$_2$.8H$_2$O, SrCl$_2$, Sr(CN)$_2$.4H$_2$O, SrS$_2$O$_6$.4H$_2$O, SrF$_2$, Sr[SiF$_6$].2H$_2$O, Sr(HCO$_2$)$_2$, Sr(HCO$_2$)$_2$.2H$_2$O, Sr(SH)$_2$, Sr(OH)$_2$, Sr(OH)$_2$.8H$_2$O, Sr(IO$_3$)$_2$, SrI$_2$, SrI$_2$.6H$_2$O, Sr(NO$_3$)$_2$, Sr(NO$_3$)$_2$.4H$_2$O, Sr(NO$_2$)$_2$, Sr(NO$_2$)$_2$.H$_2$O, SrC$_2$O$_4$.H$_2$O, SrO, SrO$_2$, SrO$_2$.8H$_2$O, Sr(MnO$_4$)$_2$.3H$_2$O, SrHPO$_4$, SrSiO$_3$, SrSO$_4$, Sr(HSO$_4$)$_2$, SrS, SrS$_4$.6H$_2$O, SrSO$_3$, Sr(CNS)$_2$.3H$_2$O, SrS$_2$O$_3$.5H$_2$O, Ba, Ba(C$_2$H$_3$O$_2$)$_2$, Ba(C$_2$H$_3$O$_2$)$_2$.H$_2$O, Ba(NH$_2$)$_2$, Ba$_3$(AsO$_4$)$_2$, BaHAsO$_4$.H$_2$O, Ba(N$_3$)$_2$, Ba(N$_3$)$_2$.H$_2$O, Ba(BrO$_3$)$_2$.H$_2$O, BaBr$_2$, BaBr$_2$.2H$_2$O, Ba[PtBr$_6$].10H$_2$O, BaC$_2$, BaCO$_3$, Ba(ClO$_3$)$_2$, Ba(ClO$_3$)$_2$.H$_2$O, BaCl$_2$, BaCl$_2$.2H$_2$O, Ba(CN)$_2$, BaS$_2$O$_6$.2H$_2$O, BaF$_2$, Ba[SiF$_6$], Ba(HCO$_2$)$_2$, BaH$_2$, Ba(SH)$_2$.4H$_2$O, Ba(OH)$_2$, Ba(OH)$_2$.8H$_2$O, Ba(ClO)$_2$, BaPO$_3$, Ba(H$_2$PO$_2$)$_2$.H$_2$O, Ba(IO$_3$)$_2$, Ba(IO$_3$)$_2$.H$_2$O, BaI$_2$.2H$_2$O, BaI$_2$.6H$_2$O, BaMnO$_4$, BaMoO$_4$, Ba(NO$_3$)$_2$, Ba(NO$_2$)$_2$, Ba(NO$_2$)$_2$.H$_2$O, BaC$_2$O$_4$, BaO, Ba(ClO$_4$)$_2$, Ba(ClO$_4$)$_2$.3H$_2$O, Ba(MnO$_4$)$_2$, BaO$_2$, BaO$_2$.8H$_2$O, BaS$_2$O$_8$.4H$_2$O, BaHPO$_4$, Ba(H$_2$PO$_4$)$_2$, Ba$_2$P$_2$O$_7$, Ba$_3$(PO$_4$)$_2$, BaSiO$_3$, BaSiO$_3$.6H$_2$O, BaSO$_4$, BaS, BaS$_4$.2H$_2$O, BaS$_3$, BaSO$_3$, Ba(CNS)$_2$.2H$_2$O, BaS$_2$O$_3$.H$_2$O.

Since a halide, such as a bromide or an iodide is used and the object product is a carboxylic acid, it is preferable that the promoter metal be used in form of a halide, such as bromide or iodide, or organic acid salt, such as acetate.

The amount of metals of Group IVB or compounds of the metals employed as component (i) constituting the promoter may be in the range of 0.01 g-atom–100 g-atom, preferably 0.03 g-atom–30 g-atom, more preferably 0.1 g-atom–20 g-atom and most preferably 0.5 g-atom–10 g-atom per 1 g-atom of the catalyst in terms of metal. However, in general, the amount of component (i) employed may be in the range of $10^{-5}$ g-atom–4 g-atom, preferably $10^{-4}$ g-atom–1 g-atom and most preferably $10^{-3}$ g-atom–0.25 g-atom per 1 liter of a reaction solution in terms of metal. In general, the amount of the metal of Group IA or IIA or compound of the metal employed as component (ii)(b) constituting the promoter may be in the range of 0.01 g-atom–100 g-atom, preferably 0.03 g-atom–30 g-atom and most preferably 0.1 g-atom–20 g-atom per g-atom of the catalyst in terms of metal. In general, the amount of component (ii)(b) employed may be in the range of $10^{-4}$ g-atom–30 g-atom, preferably $10^-$g-atom–10 g-atom and most preferably $10^{-2}$ g-atom–3 g-atom per 1 liter of a reaction solution.

Within the limitation as mentioned above, the amount of component (ii)(b) employed may be in the range of $10^{-3}$ g-atom– $10^{-3}$ g-atom, preferably $10^{-2}$ g-atom–$10^2$ g-atom and most preferably 0.1 g-atom–50 g-atom per 1 g-atom of component (i) in terms of metal.

Alternatively, the promoter of this invention may contain component (i) and an organic nitrogen compound (ii)(a).

Examples of the organic nitrogen compounds are shown in the following. However, compounds which are not listed in the following may be used as a promoter.

(I) Compounds of a trivalent nitrogen element
(A) Compounds represented by the formula

(a) compounds wherein $R^1$, $R^2$ and $R^3$ may be the same or different, and are independently hydrogen, saturated alkyl having 1–10 carbon atoms, saturated cycloalkyl having 3–10 carbon atoms, or aryl having 6–10 carbon atoms.

The compounds include, for example, amines, such asmonomethyl amine, dimethyl amine, trimethyl amine, monoethylamine, diethyl amine, triethyl amine, dimethyl ethyl amine, tri-n-propyl amine, tri-iso-propyl amine, tri-n-butyl amine, tri-tert.-butyl amine, aniline, dimethyl aniline, diethyl aniline, dimethyl-benzyl amine, toluidine, triphenyl amine, cyclohexyl amine and the like.

(b) Wherein $R^1$ is hydrogen, alkyl having 1–10 carbon atoms, cycloalkyl having 3–10 carbon atoms, or aryl and $R^2$ and $R^3$ are taken together and represents methylene or polymethylene having 2–5 carbon atoms; the compounds include, for example, pyrrolidine, N-methyl pyrrolidine, piperidine or N-phenyl piperidine:

(c) Wherein $R^1$ and $R^2$ may be the same or the different and independently represent hydrogen, alkyl having 1–10 carbon atoms, cycloalkyl having 3–10 carbon atoms, or aryl and having 6–10 carbon atoms and $R^3$ is aliphatic saturated acyl, or $R^1$ is hydrogen, alkyl having 1–10 carbon atoms, cycloalkyl having 3–10 carbon atoms or aryl having 6–10 carbon atoms, and $R^2$ and $R^3$ are taken together and represent lactam ring (in which $R^2$ and $R^3$ are bonded through carboxy polymethylene); the compounds include, for example carboxylamides such as acetamide, N,N-dimethylacetamide, acetanilide, N-methyl-N-phenylacetamide, and lactams, such as N-methylpyrrolidinone:

(d) Wherein at least one of $R^1$, $R^2$ and $R^3$ is carboxymethyl and the remainder is hydrogen, alkyl having 1–10 carbon atoms, cycloalkyl having 3–10 carbon atoms or aryl having 6–10 carbon atoms; the compounds include, for example carboxylic acid derivatives, such as N,N-dimethyl glycine, N,N-diethyl glycine, iminodiacetic acid, N-methyl iminodiacetic acid, or nitrilotriacetic acid:

(B) Organic compounds represented by the formula N≡CR wherein R represents an alkyl having 1 to 10 carbon atoms, a cycloalkyl having 3–10 carbon atoms or aryl; the compounds include, for example, nitriles, such as acetonitrile, propio-nitrile or benzonitrile.

(C) Organic nitrogen compounds represented by the formula

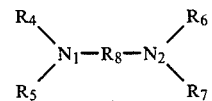

(a) Wherein $R^4$, $R^5$, $R^6$ and $R^7$ may be the same or different and independently hydrogen, alkyl having 1–10 carbon atoms, cycloalkyl having 3–10 carbon atoms, or aryl and $R^8$ is methylene group or polymethylene group having 2–10 carbon atoms, phenylene, or carbonyl group.

The compounds include, for example, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetramethyl urea, N-methyl-2-pyrrodinone and triethylenediamine.

(b) $R^4$ and $R^6$ may be the same or different and independently represent hydrogen, alkyl having 1–10 carbon atoms, cycloalkyl having 3–10 carbon atoms or aryl and $R^5$ and $R^7$ are taken together and represent methylene or polymethylene having 2–5 carbok toms and $R^8$ is methylene or polymethylene having 2–5 carbon atoms; the compounds include, for example, heterocyclic compounds, such as piperazine, N-methyl-piperazine, N-ethylpiperazine, or 2-methyl-N,N'-dimethylpiperazine.

(c) Other compounds include, for example, tris(diethylaminomethyl)stibine, 2,5-dicarboxy-piperazine, cyclohexane-1,2-diamine-N,N,N',N'-tetraacetic acid or salts thereof, tetramethylester thereof, ethylenediaminetetraacetic acid, or its salt or tetramethylester thereof, 1,4-azabicyclo[2,2,2]octane, methyl substituted 1,4-diazabicyclo[2,2,2]octane, adiponitrile or N-methylmorpholine.

(II) Hetero cyclic compounds include, for example, pyridines, such as pyridine; α-picoline, β-picoline, γ-picoline, 2-ethylpyridine, 3-ethylpyridine, 4-ethylpyridine, 2-propylpyridine, 4-propylpyridine, 4-butylpyridine, 4-isobutylpyridine, 4-tert.-butylpyridine, 2,6-lutidine, 2,4-lutidine, 2,5-lutidine, 3,4-lutidine, 3,5-lutidine, 2,4,6-collidine, 2-methyl-4-ethylpyridine, 2-methyl-5-ethylpyridine, 3-methyl-4-ethylpyridine, 3-ethyl-4-methylpyridine, 3,4-diethylpyridine, 3,5-diethylpyridine, 2-methyl-5-butylpyridine, 4-pentylpyridine, 4-(5-nonyl)pyridine, 2,6-dipropylpyridine, 2-methyl-3-ethyl-6-propylpyridine, 2,6-diethylpyridine, 2,6-dipropylpyridine, 2,6-dibutylpyridine, 2,6-di-tert.-butylpyridine; functional group-containing pyridines; such as 2-cyanopyridine, 3-cyanopyridine, 4-cyanopyridine, 2,6-dicyanopyridine, 3,5-dicyanopyridine, 2-cyano-6-methylpyridine, 3-cyano-5-methylpyridine, picolinic amide, nicotinic amide, isonicotinic amide, picolinic acid, nicotinic acid, isonicotinic acid, dipicolinic acid, dinicotinic acid, cinchomethorinic acid, 5-butyl-picolinic acid, alkyl esters of nicotinic acid, 2-aminopyridine, 3-aminopyridine, 4-aminopyridine, 2,3-diaminopyridine, 2,5-diaminopyridine, 2,6-diaminopyridine, 2,3,6-triaminopyridine, 2-amino-3-methylpyridine, 2-amino-4-methylpyridine, 2-amino-5-methylpyridine, 2-amino-6-methylpyridine, 2-amino-4-ethylpyridine, 2-amino-4-propylpyridine, 2-amino-4-(5-nonyl)pyridine, 2-amino-4,6-dimethylpyridine, 2,6-diamino-4-methylpyridine, 2,2'-dipyridylamine, 4-(N,N-dimethylamino)pyridine, 2-hydroxypyridine, 3-hydroxypyridine, 4-hydroxypyridine, 2,6-dihydroxypyridine, 3-hydroxy-6-methylpyridine, 2-chloropyridine, 2,6-dichloropyridine, 4-chloropyridine, 2-amino-5-chloropyridine, 2-amino-3,5-dichloropyridine, 2-methyl-3,5-dichloro-6-methylpyridine, 2-amino-5-chloro-3-methylpyridine, 2-amino-3,5-dichloro-4-methylpyridine, 2-amino-3,5-dichloro-4,6-dimethylpyridine, 4-amino-3,5-dichloropyridine, pyridine-N-oxide, α-picoline-N-oxide, β-picoline-N-oxide, γ-picoline-N-oxide, 2,6-lutidine-N-oxide, 3,5-lutidine-N-oxide, 4-phenylpropylpyridine-N-oxide, 1,3-di(4-pyridyl)propane-di-N-oxide, 4-(5-nonyl)pyridine-N-oxide, 2-chloropyridine-N-oxide, 4-cyanopyridine-N-oxide, 2-pyridinemethanol-N-oxide, 3-pyridinemethanol, 4-pyridinemethanol, 2,6-pyridinemethanol, 2-pyridineethanol, 4-pyridineethanol, 3-picolyamine, 4-picolyamine, 2-methylaminoethylpyridine, 4-alkylaminoethyl-pyridines, 4-piperidinoethylpyridine, 4-(4-pipecolinoethyl)-pyridine, and 4-morpholinoethylpyridine, pyridines containing heterocyclic or homocyclic group, such as 2-phenylpyridine, 4-phenylpyridine, 2-benzylpyridine, 4-benzylpyridine, 4-phenylpropylpyridine, 4,4'-dipyridyl, 4,4'-dimethyl-2,2'-dipyridyl, 1,3-di(4-pyridyl)propane, 1,2-di(4-pyridyl)ethane, 1,2-di(4-pyridyl)ethylene, 1,2,3-tri(4-pyridyl)propane, 2,4,6-tri(4-pyridyl)-S-triazine, 2,4-di(4-pyridyl)-6-methyl-S-triazine, and 2,5-di(4-pyridyl)-S-tetrazine, alkenylpyridines or polymer pyridines, such as 2-vinylpyridine, 4-vinylpyridine, 2-vinyl-6-methylpyridine, 2-vinyl-5-ethylpyridine, 4-butenyl pyridine, pyridine, 4-vinylpyridine homopolymer, 2-vinylpyridine homopolymer, 2-vinylpyridineacrylonitrile copolymer, 4-vinylpyridine-acrylonitrile copolymer, 4-vinylpyridine-styrene copolymer, 4-vinylpyridinedivinylbenzene copolymer, 2-vinylpyridine-divinylbenzene copolymer, and 4-vinylpyridine homopolymer-N-oxide; pyrroles; pyrrolines; pyrinidines; pyrazines; pyrazoles; pyrazolines; pyridazines; imidazoles; 1,10-phenanthrolines, such as 1,10-phenanthroline 4-chloro-1,10-phenanthroline, and 5-(thiabentyl)-1,10-phenanthroline; quinolines, such as quinoline, 2-(dimethylamino)-6-methoxyquinoline, 8-hydroxyquinoline and 2-carboxyquinoline.

Of these nitrogen compounds, carboxylic acid amides and heterocyclic compounds containing trivalent nitrogen atom, such as pyridines, or onium salts of the compounds are most preferable.

The amount of the organic nitrogen compound employed as one component of the catalyst depends upon the kind and amount of the catalyst. However, in general, the amount of the compounds employed may be in the range of $10^{-6}$ mol–10 mol, preferably $10^{-4}$ mol–5 mol and most preferably $10^{-3}$ mol–2.5 mol per 1 liter of a reaction solution.

The promoter may comprise component (i) and combination of component (ii)(a) and component (ii)(b). The promoters comprising components (i), (ii)(a) and (ii)(b) increase the rate of reaction.

In practicing this invention, the reaction temperature is not critical. In general, the reaction temperature may be within the range of 20° C.–350° C., preferably 80° C.–300° C. and most preferably 100° C.–250° C.

The reaction pressure is kept high enough to keep the raw material(s), the solvent and the product in a liquid phase and to maintain appropriately partial pressure of carbon monoxide. The partial pressure of carbon monoxide may be in the range of 0.5 Kg/cm$^2$–300 Kg/cm$^2$, preferably 1 Kg/cm$^2$–200 Kg/cm$^2$, and most preferably 3 Kg/cm$^2$–150 Kg/cm$^2$. However, partial pressure of the carbon monoxide may be in the range of 0.05 Kg/cm$^2$–5,000 Kg/cm$^2$.

The hydrocarbyl alcohols employed as a starting material in this invention may be hydrocarbyl alcohols having 1–11 carbon atoms. Examples of the alcohols include, for example methanol, ethanol, propanol, butanol, pentanol, hexanol, decanol and benzyl alcohol.

The reactions for producing a carboxylic acid from a hydrocarbyl alcohol and carbon monoxide can be expressed as follows:

$$CO + ROH \rightarrow RCOOH \qquad (1)$$

wherein R is alkyl having 1-10 carbon atoms, aryl having 6-10 carbon atoms, or benzyl. For example, acetic acid can be produced from methanol and carbon monoxide and propionic acid can be produced from ethanol and carbon monoxide.

Alternatively, carboxylic acid esters and ethers can be used as a starting material in place of the hydrocarbyl alcohol. In these cases, the reactions can be expressed as follows:

$$CO + RCOOR + H_2O \rightarrow 2RCOOH \quad (2)$$

$$2CO + ROR + H_2O \rightarrow 2RCOOH \quad (3)$$

wherein R is as defined above. For example, acetic acid can be produced from methyl acetate or dimethyl ether and carbon monoxide.

The carbon monoxide employed as a raw material gas does not need to be highly pure and may contain hydrogen, carbon dioxide, methane, nitrogen and rare gases. Hydrogen does not interfere with the carbonylation reaction but, rather, stabilizes the catalyst, and advantageously proceeds the reaction. An extremely low concentration of carbon monoxide in the reaction system is not desirable, because the reaction pressure must rise when using the gas.

Since hydrocarbyl alcohols, such as methanol (as a starting material) and/or carboxylic acids, such as acetic acid (object product) serves as a solvent for the reaction of this invention, another solvent may not be used. Any organic solvent compatible with the starting material and the object product under the reaction conditions may be used.

Solvents which participate in the reaction as a component constituting catalyst, a raw material, an intermediate, a by-product or a product are preferable. Such solvents include methyl iodide, methanol, methyl acetate, water, acetic anhydride and acetic acid, etc.

When component (i) is combined with component (ii)(b), a carboxylic acid, particularly acetic acid, is preferred since it has a tendency to stabilize the catalyst and accelerate the reaction. This is all the more true since the reaction product also serves as the reaction solvent.

In addition to the above solvents, diluents compatible with the starting material and the object product may be used in the present invention. Examples of the diluents include organic acids, such as propionic acid, butyric acid, octanoic acid, phthalic acid, and benzoic acid; organic acid esters such as methyl acetate, ethyl acetate, ethylene glycol diacetate, propylene glycol diacetate, dimethyl adipate, methyl benzoate, ethyl benzoate, dimethyl phthalate, diethyl phthalate, dioctyl phthalate, phenyl acetate and tolyl acetate; hydrocarbons, such as dodecane, hexadecane, benzene, naphthalene, and biphenyl; inorganic acid esters, such as triphenyl phosphate, tricresyl phosphate, dibutylphenyl phosphate, tetramethyl orthosilicate and tetrabutyl silicate, aromatic ethers, such as diphenyl ether; and ketones, such as acetone, methyl ethyl ketone, dibutyl ketone, methyl isobutyl ketone, acetophenone and benzophenone.

Acetic acid and acetic anhydride can simultaneously be produced from methanol and methyl acetate or dimethyl ether by maintaining the reaction system under substantially anhydrous conditions.

The present process may be carried out by batch, semicontinuous or continuous method.

The present invention is characterized by production of a carboxylic acid by reaction of a hydrocarbyl alcohol and carbon monoxide by using highly active nonexpensive catalyst, so the present invention is preferable from an industrial point of view.

The following examples are given as illustrative embodiment of the invention and should not be construed as limiting its scope.

The term "formation rate of carboxylic acid" as used in the Examples means the amount of carboxylic acid yielded per gram of elemental catalyst metal per gram of elemental halogen per hour as represented by the equation $$\text{formation rate of carboxylic acid} = \frac{\text{carboxylic acid (g) formed}}{[\text{metal (g) used}] \times [\text{halogen (g) used}] \times [\text{hour}]}$$

EXAMPLE 1

Into a tantalum-clad autoclave were charged 25.6 g of methanol, 24.0 g of acetic acid, 0.208 g of nickel powder, 6.8 g of methyl iodide, 1.67 g of stannous acetate, and 5.28 g of lithium acetate. After the temperature was raised to 180° C., carbon monoxide was fed under pressure to a pressure of 80 Kg/cm² (partial pressure of H₂ is 10 Kg/cm² and partial pressure of CO is 54 Kg/cm²). The reaction of methanol and carbon monoxide was carried out at 180° C. for 1.5 hours while maintaining the pressure at 80 Kg/cm² by continuously feeding carbon monoxide into the autoclave. After cooling the reaction mixture, analysis showed that the yield of acetic acid was 88.5% on the basis of methanol.

EXAMPLES 2-8

The reactions of methanol and carbon monoxide were carried out in the same way as in Example 1.

The feeding materials, reaction conditions and results are shown in Table 1.

TABLE 1

| Ex. No. | Starting Material (g) | Solvent (g) | Nickel Catalyst (g) | Halide (g) | Promoter (g) | | Reaction Conditions | | | Time (hr) | Yield of Acetic Acid (%) | Formation Rate of Acetic Acid (g) / [Ni or Co;g]·[I;g][Hr] |
|---|---|---|---|---|---|---|---|---|---|---|---|---|
| | | | | | | | Temperature (°C.) | Total Pressure (Kg/cm²) | Partial Pressure of CO(H₂) (Kg/cm²) | | | |
| 1 | MeOH 25.6 | AcOH 24.0 | Ni powder 0.208 | CH₃I 6.8 | Sn(OAc)₂ 1.67 | LiOAc 5.28 | 180 | 80 | 54(10) | 1.5 | 88.5 | 22.4 |
| 2 | MeOH 12.8 | AcOH 24.0 | Ni powder 0.208 | CH₃I 14.0 | Sn(OAc)₂ 1.67 | LiOAc 2.64 | 180 | 80 | 54(10) | 0.5 | 98.2 | 18.1 |
| 3 | MeOH 12.8 | AcOH 24.0 | NiI₂ 1.11 | CH₃I 12.0 | Sn(OAc)₂ 1.67 | Sr(OAc)₂ 8.22 | 180 | 60 | 38(10) | 1.5 | 82.3 | 4.9 |
| 4 | MeOH | AcOφ | Ni powder | CH₃I | SnI₄ | LiOAc | 180 | 60 | 34(10) | 0.5 | 87.2 | 16.1 |

TABLE 1-continued

| Ex. No. | Starting Material (g) | Solvent (g) | Nickel Catalyst (g) | Halide (g) | | Promoter (g) | Temperature (°C.) | Reaction Conditions Total Pressure (Kg/cm²) | Partial Pressure of CO(H₂) (Kg/cm²) | Time (hr) | Yield of Acetic Acid (%) | Formation Rate of Acetic Acid (g) / [Ni or Co;g]·[I;g][Hr] |
|---|---|---|---|---|---|---|---|---|---|---|---|---|
| 5 | MeOH 25.6 | AcOH 24.0 | Ni powder 0.416 | CH₃I 12.0 | Sn(OAc)₂ 1.67 | LiI 2.68 | 180 | 60 | 30(10) | 1.0 | 88.1 | 7.7 |
| 6 | EtOH 18.4 | EtCOOH 24.0 | Ni powder 0.208 | EtI 15.0 | SnI₄ 4.43 | LiI 5.36 | 190 | 80 | 54(10) | 1.5 | EtCOOH 72.3 | EtCOOH 3.4 |
| 7 | MeOH 12.8 | AcOH 24.0 | Co₂(CO)₈ 2.6 | CH₃I 14.0 | Sn(OAc)₂ 1.67 | LiOAc 2.64 | 200 | 190 | 140(20) | 5.0 | 52.3 | 0.2 |
| 8 | MeOH 12.8 | AcOH 24.0 | Ni powder 0.208 | CH₃I 13.0 | SnI₄ 3.75 | LiOAc 3.90 | 190 | 80 | 50(10) | 1.0 | 87.4 | 6.6 |

EXAMPLE 9

Into a tantalum-clad autoclave were charged 25.6 g of methanol, 24.0 g of acetic acid, 0.415 g of nickel powder, 1.52 g of 2,4-lutidine, 14 g of methyl iodide and 4.43 g of stannous iodide. After the temperature was raised to 180° C., carbon monoxide was fed under pressure to pressure of 80 Kg/cm²·G (partial pressure of H₂ is 10 Kg/cm² and partial pressure of CO is 55 Kg/cm²). The reaction of methanol and carbon monoxide was carried out at 180° C. for 2 hours while maintaining the pressure at 80 Kg/cm² by continuously feeding carbon monoxide into the autoclave. After cooling the reaction mixture, analysis showed that yield of acetic acid was 96.5% on the basis of methanol.

EXAMPLES 10-19

The reactions of methanol and carbon monoxide were carried out in the same way as in Example 9.

The feeding materials, reaction conditions and results are shown in Table 2.

TABLE 2

| Ex. No. | Starting Material (g) | Solvent (g) | Nickel Catalyst (g) | Organic Nitrogen Group Compound (g) | Halide (g) | | Promoter (g) | Temperature (°C.) | Reaction Conditions Total Pressure (Kg/cm²) | Partial Pressure of CO(H₂) (Kg/cm²) | Time (hr) | Yield of Acetic Acid (%) | Formation Rate of Acetic Acid (g) / [Ni or Co;g]·[I;g][Hr] |
|---|---|---|---|---|---|---|---|---|---|---|---|---|---|
| 9 | MeOH 25.6 | AcOH 24.0 | Ni powder 0.415 | 2,4-lutidine 1.52 | CH₃I 14.0 | SnI₄ 4.43 | | 180 | 80 | 55(10) | 2.0 | 96.5 | 3.5 |
| 10 | MeOH 25.6 | AcOH 24.0 | Ni powder 0.415 | 2,6-lutidine 1.52 | CH₃I 14.0 | SnI₄ 4.43 | LiOAc 2.64 | 180 | 70 | 45(10) | 1.0 | 96.1 | 6.9 |
| 11 | MeOH 12.8 | AcOφ 30.0 | Ni powder 0.415 | (n-Bu)₃N 2.62 | CH₃I 14.0 | Sn(OAc)₂ 1.67 | LiOAc 2.64 | 200 | 30 | 10(0) | 1.0 | 92.5 | 4.3 |
| 12 | MeOH 12.8 | AcOH 24.0 | NiI₂ 2.21 | 2,4-lutidine 1.52 | CH₃I 14.0 | Si(OCH₃)₄ 1.08 | SrI₂ 13.7 | 180 | 80 | 55(10) | 3.5 | 91.0 | 0.6 |
| 13 | MeOH 12.8 | Acφ 30.0 | Ni powder 0.415 | N,N—dimethyl acetamide 1.23 | CH₃I 10.0 | SnHPO₄ 1.52 | | 200 | 40 | 17(3) | 0.5 | 95.3 | 12.3 |
| 14 | MeOH 25.6 | Ac₂O 24.0 | Ni powder 0.415 | α-picoline 1.32 | CH₃I 14.0 | SnI₄ 2.63 | LiOAc 2.64 | 190 | 40 | 20(0) | 1.5 | 96.2 | 5.2 |
| 15 | EtOH 18.4 | EtCOOH 30.0 | Ni powder 0.415 | 2,4-lutidine 1.52 | EtI 15.6 | SnI₄ 4.43 | LiOAc 2.64 | 180 | 80 | 55(10) | 2.0 | 81.0 | 1.1 |
| 16 | MeOH 25.6 | AcOMe 24.0 | NiI₂ 2.21 | 2,4-lutidine 1.52 | | SnI₄ 4.43 | CaI₂ 14.7 | 180 | 60 | 40(5) | 1.5 | 97.2 | 4.4 |
| 17 | MeOH 25.6 | AcOH 24.0 | Ni powder 0.415 | 2,4,6-trimethyl pyridine 3.42 | AcI 17.0 | Sn(OAc)₂ 1.67 | SrI₂ 6.9 | 165 | 70 | 50(10) | 2.0 | 95.1 | 3.1 |
| 18 | MeOH 25.6 | AcOH 24.0 | Ni powder 0.830 | 2,4-lutidine 3.04 | CH₃I 12.0 | SnI₄ 4.43 | LiOAc 5.28 | 195 | 40 | 20(3) | 0.5 | 97.6 | 7.9 |
| 19 | MeOH 12.8 AcOMe 22.2 H₂O 5.4 | AcOH 24.0 | Ni powder 0.623 | 2,6-lutidine 2.28 | CH₃I 13.0 | SnI₄ 4.43 | LiOAc 5.28 | 180 | 60 | 40(5) | 1.0 | 92.7 | 4.1 |

EXAMPLE 20

Into a 500 ml autoclave equipped with liquid-withdrawing means were charged components of (about 400 ml) of Example 1. The reaction was started at 180° C. and 80 Kg/cm$^2$·G (partial pressure of CO is 54 Kg/cm$^2$ and partial pressure of H$_2$ is 10 Kg/cm$^2$). The starting material, the solvent, the catalyst, the halide and the promoter were continuously fed into the autoclave and the reaction mixture was continuously withdrawn so that conversion of methanol to acetic acid was maintained at 92.5%. Acetic acid was continuously separated from the unreacted starting material, the catalyst, the solvent, the halide and the promoter by distillation. The components other than acetic acid withdrawn from the autoclave were circulated into the autoclave. The reaction was continued for 24 hours. Methanol was fed at rate of 38.4 g/hr and acetic acid was formed at an average rate of 72 g/hr. During the reaction, the catalyst, the halide and the promoter were not deteriorated and by-products were not formed.

Control run 1

This run was carried out according to Example 1 of U.S. Pat. No. 4,134,912.

Into an autoclave were charged 32 g (1 mol, 31.4 wt %) of methanol, 45.4 g (0.32 mol, 44.5 wt %) of methyl iodide, 5.0 g (0.02 mol, 4.9 wt %) of nickel diacetate tetrahydrate and 19.6 g (0.046 mol, 19.2 wt %) of tetraphenyl tin. The reaction was carried out in the same way as in Example 1. After 14 hrs. the analysis was carried out. The analysis showed that the yield of methyl acetate was 28.7% and the yield of acetic acid was 5.8% on the basis of methanol. The formation rate of acetic acid was 0.031 [g]/[Ni;g][I;g][Hr]. After the reaction had been completed, a large amount of crystal derived from tetraphenyl tin was precipitated.

Control run 2

This run was based on Example 1 of Japanese Patent Publication (kohkai) No. 84912/1978.

Into an autoclave were charged 16.6 g (0.52 mol, 14.0 wt %) of methanol, 35.5 g (0.48 mol, 29.9 wt %) of methyl acetate, 46.9 g (0.33 mol, 39.5 wt %) of methyl iodide, 2.12 g (0.12 mol, 1.8 wt %) of water, 13.4 g (0.021 mol, 11.3 wt %) of bisphenylphosphine nickeldicarbonyl and 4.2 g (0.016 mol, 3.5 wt %) of triphenyl phosphine. The reaction was carried out at 150° C. and 52 Kg/cm$^2$ (partial pressure of CO is 45 Kg/cm$^2$) for 5.5 hours. Analysis showed that 30.6 g of acetic acid was formed by carbonylation. This means that the yield of acetic acid was 51% on the basis of the starting material. When the reaction was completed, a large amount of crystal derived from triphenyl phosphine was precipitated. The formation rate of acetic acid was 0.11 [g]/[Ni;g][I;g][Hr].

Control run 3

This run was based on Example 2 of Japanese Patent Publication (kohkai) No. 84912/1978.

Into an autoclave were charged 24.3 g (0.76 mol, 23.3 wt %) of methanol, 17.8 g (0.24 mol, 17.0 wt %) of methyl acetate, 46.9 g (0.33 mol, 44.9 wt %) of methyl iodide, 13.4 g (0.021 mol, 12.8 wt %) of bistriphenyl phosphine nickel dicarbonyl and 2.10 g (0.008 mol, 2 wt %) of triphenyl phosphine. The reaction was carried out at 150° C. and 51 Kg/cm$^2$ (partial pressure of CO is 18 Kg/cm$^2$ and partial pressure of H$_2$ is 28 Kg/cm$^2$) for 2 hours. Analysis showed that the yield of methyl acetate was 8.2% and the yield of acetic acid was 60.6% on the basis of methanol. A large amount of crystal derived from triphenyl phosphine was formed. The formation rate of acetic acid was 0.31 [g]/[Ni;g][I;g][Hr].

In control runs 1, 2 and 3 iodobenzene was precipitated by decomposition of tetraphenyl tin or triphenyl phosphine.

What is claimed is:

1. A process for producing a carboxylic acid which comprises reacting a hydrocarbyl alcohol with carbon monoxide in the presence of (A), a catalyst consisting essentially of at least one material selected from the group consisting of nickel, nickel compounds and mixtures thereof, (B) at least one iodide and (C) a promotor characterized in that said promotor consists essentially of:

component (i) composed of one or more compounds selected from the group consisting of stannous iodide, stannous acetate and stannic iodide, and component (ii) composed of one or more compunds selected from the group consisting of lithium iodide and lithium actate;

wherein the amount of said component (ii) employed is in the range of 10$^{-3}$ to 10 g-atom per 1 liter of the reaction solution in terms of metal and at the same time, it is in the range of 0.01 to 100 g-atom per 1 g-atom of catalyst (A) in terms of metal; said reaction being carried out at a temperature of 80° to 300° C. and at a carbon monoxide partial pressure of 1 to 200 kg/cm$^2$.

2. The process as defined in claim 1 wherein the amount of said component (i) employed is in the range of 10$^{-5}$ to 4 g-atom per 1 liter of a reaction solution in terms of metal.

3. The process as defined in claim 1 wherein the amount of the catalyst employed is in the range of 10$^{-6}$ to 5 mol per 1 liter of the reaction solution in terms of metal.

4. The process as defined in claim 1 wherein the amount of the iodide employed is in the range of 10$^{-3}$ to 15 mol per 1 liter of the reaction solution in terms of halogen atom.

5. The process as defined in claim 1 wherein the hydrocarbyl alcohol has 1-11 carbon atoms.

6. The process as defined in claim 5 wherein the hydrocarbyl alcohol is methanol.

7. The process defined in claim 1 wherein the amount of said component (i) employed is in the range of 10$^{-4}$ to 1 g-atom per 1 liter of the reaction solution in terms of metal.

8. The process as defined in claim 1 wherein the amount of said component (i) employed is in the range of 10$^{-3}$ to 0.25 g-atom per 1 liter of the reaction solution in terms of metal.

9. The process as defined in claim 1 wherein the amount of said component (ii) employed is in the range of 10$^{-2}$ to 3 g-atom per 1 liter of the reaction solution in terms of metal.

10. The process as defined in claim 1 wherein the amount of the component (i) is in the range of 0.01 to 100 g-atom per 1 g-atom of catalyst (A) in terms of metal.

11. The process as defined in claim 1 wherein the amount of the component (i) is in the range of 0.03 to 30 g-atom per 1 g-atom of catalyst (A) in terms metal.

12. The process as defined in claim 1 wherein the amount of the component (i) is in the range of 0.1 to 20 g-atom per 1 g-atom of catalyst (A) in terms of metal.

13. The process as defined in claim 1 wherein the amount of the component (ii) is in the range of 0.03 to 30 g-atom per 1 g-atom of catalyst (A) in terms of metal.

14. The process as defined in claim 1 wherein the amount of the component (ii) is in the range of 0.1 to 20 g-atom per 1 g-atom of catalyst (A) in terms of metal.

15. The process as defined in claim 1 wherein the reaction temperature is between 100° C. and 250° C.

16. The process as defined in claim 1 wherein the partial pressure of carbon monoxide is between 3 $Kg/cm^2$ and 150 $Kg/cm^2$.

17. A process for producing a carboxylic acid which comprises reacting a hydrocarbyl alcohol with carbon monoxide in the presence of (A), a catalyst consisting essentially of at least one material selected from the group consisting of nickel, nickel compounds and mixtures thereof, (B) at least one iodide and (C) a promotor characterized in that said promotor consists essentially of:

component (i) composed on one or more compounds selected from the group consisting of stannous iodide, stannous acetate and stannic iodide, and component (ii) composed of one or more compounds selected from the group consisting of lithium iodide and lithium acetate; and component (iii) composed of at least one compound selected from the group consisting of 2,6-lutidine and α-picoline;

wherein the amount of said component (ii) employed is in the range of $10^{-3}$ g-atom per 1 liter of the reaction solution in terms of metal and at the same time, it is in the range of 0.01 to 100 g-atom per 1 g-atom of catalyst (A) in terms of metal and wherein the amount of component (iii) is in the range of $10^{-6}$ to 10 mol. per liter of the reaction solution; said reaction being carried out at a temperature of 80° to 300° C. and at a partial carbon monoxide pressure of 1 to 200 $Kg/cm^2$.

* * * * *